United States Patent [19]

Miyauchi et al.

[11] 4,051,011
[45] Sept. 27, 1977

[54] CONTINUOUS ENZYMATIC REACTOR

[75] Inventors: Terukatsu Miyauchi, Yokohama; Shintaro Furusaki, Zushi, both of Japan

[73] Assignee: W. L. Gore & Associates, Inc., Newark, Del.

[21] Appl. No.: 624,901

[22] Filed: Oct. 22, 1975

[30] Foreign Application Priority Data

Oct. 26, 1974 Japan .................................. 49-123699

[51] Int. Cl.$^2$ .......................... C25B 7/00; C25B 9/00; C12B 1/00
[52] U.S. Cl. ........................ 204/299 R; 195/63; 195/116; 195/127; 195/139; 204/180 R
[58] Field of Search ................... 204/180 R, 181, 299, 204/300, 180 G, 180 S, 1 E; 23/230 B; 195/63, DIG. 11, 127, 116, 139; 427/2, 3; 428/15, 421, 543

[56] References Cited

U.S. PATENT DOCUMENTS

| | | | |
|---|---|---|---|
| 3,839,175 | 10/1974 | Keyes | 204/181 |
| 3,843,443 | 10/1974 | Fishman | 195/63 |
| 3,948,745 | 4/1976 | Guilbault et al. | 204/195 B |

*Primary Examiner*—Arthur C. Prescott
*Attorney, Agent, or Firm*—E. A. Uebler; J. S. Campbell

[57] ABSTRACT

The present invention provides an effective process for an enzymatic reaction which utilizes the enzyme membrane of the invention. The enzyme membrane consists of an enzyme strongly entrapped in a membrane base, said base being porous, fibrous, or roughened material which is permanently self-polarized or maintained polarized under an electric field. This enzyme membrane catalytically reacts with a substrate solution without loss of enzyme. The most preferred material for the membrane substrate is expanded porous polytetrafluoroethylene.

16 Claims, 1 Drawing Figure

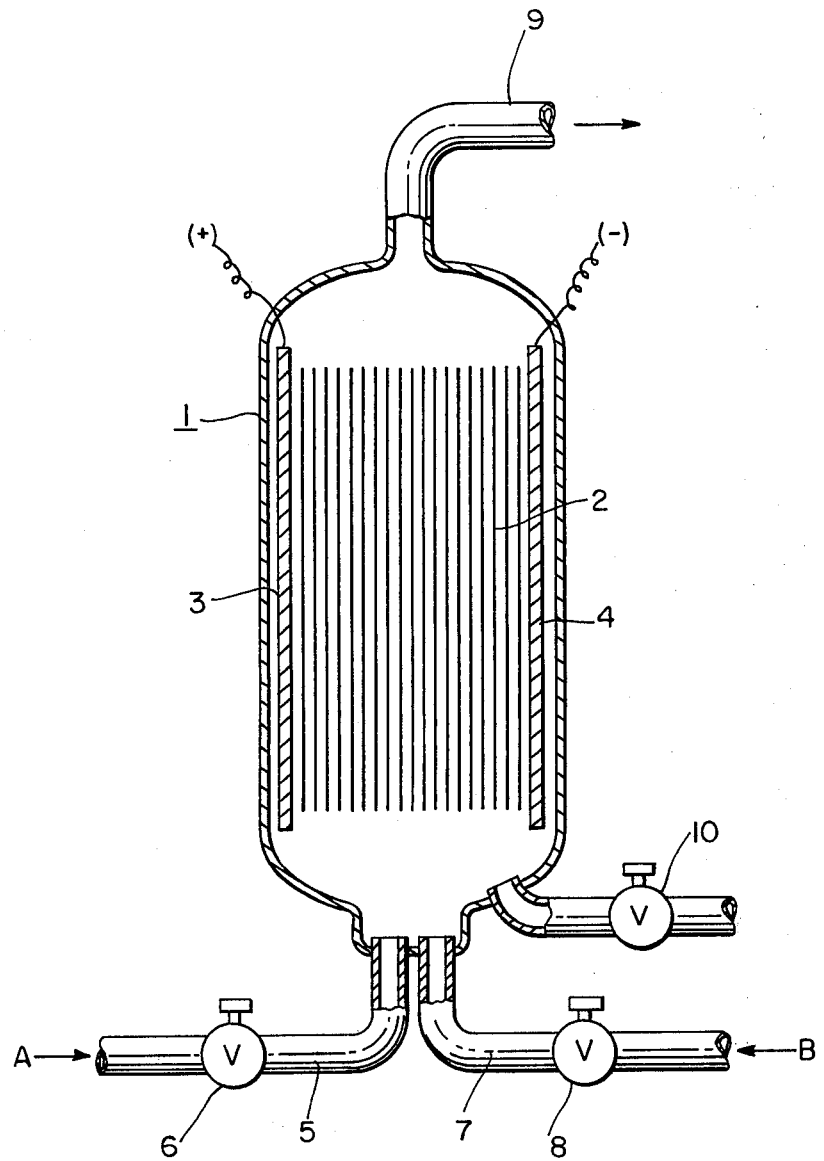

CONTINUOUS ENZYMATIC REACTOR

BACKGROUND OF THE INVENTION

1. Field of the Invention

The present invention relates to an enzymatic reaction process and membrane, and more particularly, to a process for an enzymatic reaction in which a substrate solution is brought into contact with an enzyme membrane, and in particular, an enzyme membrane having an enzyme electrically entrapped therein.

2. Description of the Prior Art

Prior art enzymatic reactions are generally carried out by adding an enzyme to a substrate solution, letting them react with each other, deactivating the residual enzyme in the reaction product at the termination of reaction, and thus obtaining a primary product. In such prior processes, the deactivated enzyme constitutes a loss. This is quite uneconomical due to the comparatively high cost of enzymes. In addition, most conventional enzyme reactions are run in batch processes.

However, at least one conventional enzymatic reaction process which is continuous has already been used. This continuous process utilizes an insoluble enzyme (or fixed enzyme) in which the enzyme is chemically bonded to a carrier. The insoluble enzyme does not mix in the reaction product, so that the enzyme efficiency is increased, and the process in continuous. This conventional continuous process has the following defects: the reaction rate of the process is lower than that of an untreated enzyme; the enzyme characteristics are liable to change, and hence a skilled engineer is required in setting up the reaction conditions; they are unsuitable for large scale industrial applications owing to the difficulties in handling the fine granules of enzyme, etc. Moreover, although the physical fixation of the enzyme is readily accomplished, the fixed enzyme releases easily.

Another conventional method of continuous enzymatic reaction has been developed, in which both substrate and enzyme solutions are contained in a dialyzing membrane bag for reaction, and their reaction product is dialyzed into the solution outside the bag. However, since this reaction requires much time to dialyze the reaction product, the overall efficiency of the reaction is low. Furthermore, problems such as clogging of the membrane are apt to occur.

SUMMARY OF THE INVENTION

The present invention provides a continuous enzymatic reaction process with high efficiency and a membrane suitable for this process, based upon a novel concept completely differing from the conventional concepts of the processes mentioned above.

The membrane of the present invention has an enzyme which is electrically entrapped on the surface or in the fine pores or irregularities of the base material.

The enzymatic reaction process of the present invention is characterized in that the substrate solution is catalytically reacted with the enzyme entrapped on the carrier.

BRIEF DESCRIPTION OF THE DRAWING

The single FIGURE is a sectional view of an apparatus embodying the process of the present invention.

DETAILED DESCRIPTION OF THE INVENTION

Explanation will be made of the practical means for entrapping an enzyme in the carrier material surface layer.

1. Utilization of Electric Fields

An enzyme is dispersed in an appropriate solvent such as water with a buffer solution to give an electrically charged colloidal solution. The aqueous colloidal enzyme solution thus formed becomes negatively charged at a pH higher than the isoelectric point (pH 4 —8), and positively charged at lower pH. Electrophoresis of the charged enzyme solution takes place under the application of an electric field to the charged solution with the resulting accumulation of the colloidal particles at one electrode; either the anode or cathode depending on their electric charge. This phenomenon can be observed by a suitable electrophoresis experiment.

When the electrophoresis of the enzyme solution containing charged colloidal particles is carried out in the presence of a suitable base material (hereinafter referred to as the "carrier") which intersects the DC electric field applied to the colloidal solution, the colloidal enzyme particles collide with the carrier on their way to the electrode and adhere to it, and in due course, almost all the particles have adhered to the surface of the carrier to form a high density layer of enzyme. (Electrodes for DC electric field application may be placed either inside or outside the solution. When the electrodes are placed in the enzyme solution, the electrode toward which the colloidal particles move is considered as a type of substrate.) The surface on which colloidal particles accumulate can be opposite to the direction of the colloidal particle transport according to the principle.

The enzyme particles which adhere to the carrier cannot be stripped off easily while the electric field is applied. Therefore, the entrapped enzyme can be used in the same manner as a fixed enzyme. In this case, utilization of a carrier having the power of absorbing the enzyme after the removal of the electric field will eliminate the need for electric field application after the enzyme is once entrapped. Examples of such suitable carriers include porous materials, fibrous materials, or solid materials having a roughened surface with pore size or irregularity dimensions thereof ranging from about 100A to 10 μ. Our experiments have disclosed that the foregoing carriers can entrap an enzyme in their pores, fibrils, or irregularities, and do not necessarily need an electric field application thereafter.

The particular carrier can be selected from a wide variety of organic and inorganic materials as long as it does not impair the enzyme's character, or the reaction between enzyme and substrate. For example, the carrier may be natural or synthetic resin, metal, ceramic, etc. The shape of the carrier may be that of a plate, sheet (or film), and so on. One or more sheets of the carrier are placed in a colloidal enzyme solution in a spaced parallel arrangement and in a direction perpendicular to that of the electric field. The carriers may also be in a shape of solid or hollow ball, cylinder, pebble; or Raschig ring, or of the saddles used in a packed tower. Many such shaped carriers can be filled into the colloidal enzyme solution in an appropriate number.

Among the carriers mentioned above, porous or irregular materials such as porous synthetic resin products, natural or artificial semipermeable membranes, felt, asbestos plate, sintered glass, sintered metal, or unglazed pottery are capable of entrapping an enzyme, and are effective as a carrier of this invention. Among other materials, expanded porous polytetrafluoroethylene membrane has a fibrillated structure which allows the clinging of enzyme, excellent chemical stability, good mechanical strength, uniform and controllable pore size, easy availability in any size and shape, and thus it is highly recommended for use as the carrier of the present invention.

Too weak an electric field applied to the colloidal enzyme solution prolongs the time of electrophoresis, and too strong a field produces an enzyme sol (colloidal) which aggregates and precipitates. According to our experiments, the electrical field between electrodes should be 1 –4 volts per centimeter, and more preferably 2.5 –3.5 V/cm.

II. Utilization of Static and Inductive Electricity

When a carrier having an electric charge opposite to that of a colloidal enzyme solution is put in the electrically charged enzyme solution, the enzyme molecules strongly adhere to and are entrapped in the surface of the carrier. The carrier thus formed by the adherence of the enzyme may be used as a type of fixed enzyme.

In this instance, the carrier consisting of an insulating material, can be electrically charged by the frictional method, corona discharge method, etc. However, the use of an electret is quite effective in the present invention. An electret is a permanently polarized piece of dielectric material such as: synthetic polymers like polytetrafluoroethylene (PTFE), polyvinylidene fluoride, polyvinyl fluoride, polyvinyl chloride, nylon, polyethylene; certain natural waxes; or inorganic insulation materials. The electret is produced by irradiating the material with a beam of electrons, or γ-rays, by applying a corona discharge, or by heating the material to its melting point and placing it in a strong electric field during cooling. The electric charge thus applied can last permanently, with a sufficiently high enough voltage (in some cases, the voltage is as high as 1,000 V).

When an enzymatic solution having an electric charge opposite to that of the carrier is applied to the electretized carrier, the enzyme strongly adheres to the carrier to give a fixed enzyme effectively applicable to the enzymatic reaction.

When bringing an enzyme into contact with a porous PTFE membrane, the enzyme is readily entrapped and fixed on the membrane fibril structure in which fine nodes are interconnected by fibrils. This entrapping is easier than in the case of a uniform polymer, and the membrane obtained produces a highly effective enzymatic reaction even for substrate molecules with a high molecular weight, because the film allows quite easy permeation and diffusion of the substrate molecules. This is an unexpected feature of this invention from the viewpoint of the conventional methods.

When the electret has the same polarization as that of the colloidal enzyme, the opposite electric charge is produced on the surface of the carrier by sandwiching a sheet electret between two dielectric sheets or by inserting a rod electret into a tubular dielectric. Thus, an enzyme with the same polarization as the electret can adhere to the carrier material.

In the second method of enzyme fixation utilizing static or induced electricity, the porous and/or rough surfaced carrier previously mentioned can successfully be employed in the effective fixation of enzyme on the substrate.

According to the process of the present invention in which an enzymatic reaction is performed by bringing a substrate solution into contact with a base material carrier having an enzyme entrapped thereon; the enzyme being entrapped either by a temporary electric field or on a permanently charged base, the following advantages have been attained:

1. Since the enzyme is electrically entrapped, and adheres to the carrier surface in a strong manner, it cannot be removed from the carrier by an environmental shock, such as flow or vibration of the substrate solution. As a result of this, deactivation of the reacted solution is eliminated and hence expensive enzymes are not wasted.

2. Degradation of the enzyme due to its electrical adherence to the carrier is not seen and the enzyme adheres to the carrier in very high concentrations, so that the spontaneous enzyme activity is totally conserved and the enzymatic reaction efficiency is remarkably increased compared to that of the conventional fixed enzyme.

3. A continuous enzymatic reaction can be achieved by using a flowing substrate solution.

4. The enzyme may easily be supplied to the carrier base.

5. If it is necessary to recover the enzyme, it can readily be removed and recovered by the applications of reverse bias voltage on the base carrier.

Explanation will be made here regarding an apparatus embodying the process of the present invention using the attached drawing. An enzyme reactor 1 contains more than one carrier substrate 2 in sheet form (e.g., porous PTFE sheet) which are stretched and held in parallel to the axis of the reactor and to each other. Electrodes 3 and 4 for applying an electric field are placed on both sides of the group of carriers. A supply pipe 5 for the electrically charged colloidal enzyme solution is open at the bottom of the reactor 1, with open/shut valve 6. A supply pipe 7 is also connected to the bottom of the reactor 1, with open/shut valve 8. At the top of the reactor, a discharge tube 9 for the reacted solution is connected.

In operation, first, a charged colloidal enzyme solution A is supplied, by opening valve 6, through pipe 5 into reactor 1, until the reactor is filled with the colloidal solution, and then valve 6 is shut. Subsequently, an electric field is applied to the colloidal solution by the application of a DC voltage to electrodes 3 and 4. This electric field causes the electrophoresis of the colloidal enzyme in the fluid toward the carrier surface 2, which results in the adherence of the particles which collide with the carriers. Upon completion of the adherence, while keeping the electric field in force (however, application of the electric field is not necessary if carrier 2 itself is capable of holding an enzyme) valve 8 is opened, and a substrate solution B is continuously introduced from pipe 7 into reactor 1 at an appropriate flow rate. The said substrate solution B may be supplied into the reactor either after the enzyme solution in the reactor is discharged from discharge valve 10 or before it is discharged. In the latter case, the enzyme solution A may be forced out from discharge tube 9 at the top of the reactor by the substrate solution B. The substrate solution which enters into the reactor flows upward through the spaces formed between adjacent carriers 2. Passing through the spaces, the substrate solution reacts with the enzyme entrapped on the carrier, and the reaction product solution can be continuously discharged from top tube 9.

Valve 6 may be opened occasionally to supply fresh colloidal enzyme solution. The enzyme supplied is also entrapped on the carrier surface, and thus the enzyme activity is kept constant.

Instead of carrier 2 in a sheet form, any form of small-sized carrier such as a sphere, a cylinder, a pebble, or a Raschig ring or saddle used in a packed tower, may be charged into reactor 1. In the case of using a previously polarized carrier such as electret, the electrodes 3 and 4 may not necessarily be required depending on the carrier.

To further illustrate the present invention, the following examples are given. These examples are not to be construed as limiting the invention.

EXAMPLE 1.

A colloidal enzymatic solution with a negative charge was prepared by dissolving 3 mg of catalase into 100 ml of phosphate buffer solution of pH 7. Two 1 cm wide by 6 cm long nickel plates having a porous PTFE membrane (pore size, 2 $\mu$max.) adhered to their surface, one being for the negative and the other for positive electrode, were dipped into the colloidal enzyme solution with a parallel clearance of 1 cm, and an electrical voltage of 3 V was applied to the electrodes for about 6 hours. Then, the positive electrode was taken out from the solution, lightly washed with water, and immersed into a 0.03 mol/l $H_2O_2$ aqueous solution (pH 7). At that time, oxygen gas ($O_2$) was generated vigorously from the porous PTFE membrane on the positive electrode, exhibiting effective enzymatic reaction. The negative electrode showed no signs of enzymatic reaction.

Enzyme was not found in the solution after the reaction. That is, no enzyme elimination from the carrier occured.

EXAMPLE 2.

A carrier was made by placing a negatively polarized electret (a fluorinated ethylene propylene resin (FEP) film) inside a porous PTFE tube (ID 2 mm, OD 4 mm, length 30 mm, pore size 2 $\mu$max.), and closing both ends by adhesion. The carrier thus prepared was put in the same type solution as used in Example 1, and allowed to stand overnight at room temperature. Then, the carrier was removed from the solution, and immersed in a 0.03 mol/l $H_2O_2$ aqueous solution, and vigorous $O_2$ gas bubbling from the porous PTFE tube surface showed an effective enzymatic reaction. As in Example 1, the carrier exhibited strong enzyme absorption, but no enzyme mixed with the reaction solution due to elimination, and no drop in enzyme activity was seen.

EXAMPLE 3.

A porous PTFE-surfaced nickel electrode (positive), i.e., the same as was used in Example 1, and a non-surface-treated nickel electrode (negative) were soaked in an aqueous glucoamylase solution (20 mg/100 ml) with a negative charge. By applying voltage, the enzyme adhered to the porous membrane. The entrapped enzyme catalytically decomposed starch dissolved in a pH 5.9 phosphate buffer solution at an initial concentration of 3 mg/ml to form glucose. Alteration of the glucose formed was analyzed as a function of time by the Wilschteler-Schule method. The following table shows the results.

| time (min) | 0 | 60 | 90 | 120 | 180 |
|---|---|---|---|---|---|
| glucose conc. formed (mg/ml) | 0.08 | 0.48 | 0.68 | 0.83 | 1.10 |

EXAMPLE 4.

An electret carrier, made by the method of Example 2, was immersed in a pH 5.9 glucoamylase solution (10 mg/ml, negative charge), and left overnight. Then, the substrate was placed in a solution of starch buffered to a pH 5.9 by a phosphate buffer, and the rate of starch decomposition was measured as the change with time of the starch concentration. The following table represents the results.

| time (min) | 0 | 30 | 60 | 120 | 180 | 240 |
|---|---|---|---|---|---|---|
| glucose conc. (mg/ml) | 0.08 | 0.25 | 0.35 | 0.57 | 0.80 | 1.05 |

EXAMPLE 5.

An electret carrier made by the same method as used in Example 2 was immersed in a 10 mg/ml solution of a commercially available acylase reagent. The carrier with the fixed enzyme was put into 100 ml of N-acetyl-DL-methionine solution maintained at pH 7 by a phosphate buffer ($2 \times 10_{-2}$mol/l, negative charge), and the L-isomer was decomposed. The change with time of the conversion ratio calculated from the concentration of the L-methionine formed is shown in the following table.

| time (min) | 0 | 30 | 60 | 90 | 120 |
|---|---|---|---|---|---|
| conversion ratio (%) | 0 | 15 | 28 | 50 | 58 |

While the invention has been disclosed herein in connection with certain embodiments and certain structural and procedural details, it is clear that changes, modifications or equivalents can be used by those skilled in the art; accordingly, such changes within the principles of the invention are intended to be included within the scope of the claims below.

We claim:

1. A device for performing catalytic enzymatic reactions comprising:
   a. a reaction vessel equipped with a valved inlet port for supplying electrically charged colloidal enzyme solution, a valved inlet port for supplying reactant substrate solution, a valved drain port, and an outlet port for discharge of reacted product; and
   b. at least one carrier with enzyme entrapped thereon located inside said reaction vessel; and
   c. means for inducing a continuous electrical field across said reaction vessel such that, in operation, colloidal enzyme introduced into said reaction vessel migrates to and is held by said carrier under the potential of said electric field, which enzyme is held fixed by electrical forces during continuous enzymatic reaction of said reactant to reacted product with no substantial loss of enzyme.

2. The device of claim 1 in which said carrier is a porous polymeric material possessing pore sizes in the range of about 100A to 10 micrometers.

3. The device of claim 1 in which said carrier is a rough-surfaced solid material having irregularity dimensions ranging from about 100A to 10 micrometers.

4. The device of claim 1 in which said carrier is an expanded porous thermoplastic crystalline polymer.

5. The device of claim 1 in which said carrier is expanded porous polytetrafluoroethylene.

6. The device of claim 1 in which said electrical field is induced by means of positive and negative electrodes immersed in said reaction vessel.

7. The device of claim 1 in which said electrical field is induced by means of the carrier being an electret.

8. The device of claim 1 in which said carrier is comprised of a porous dielectric material and a permanently polarized dielectric backing.

9. The device of claim 1 in which said carrier is comprised of a porous dielectric material and a metal backing.

10. The device of claim 1 in which said carrier is in sheet form.

11. The device of claim 1 in which said carrier is in the form of a ball.

12. The device of claim 1 in which said carrier is in the form of a cylinder.

13. The device of claim 1 in which said carrier is in the form of a rod.

14. The device of claim 1 in which said carrier is in the form of a tube.

15. The device of claim 1 in which said carrier is in the form of a plate.

16. The device of claim 1 in which said carrier is in the form of a packed bed of particles.

* * * * *